(12) United States Patent
Virkar et al.

(10) Patent No.: US 11,049,596 B2
(45) Date of Patent: Jun. 29, 2021

(54) SYSTEMS AND METHODS FOR MANAGING CLINICAL RESEARCH

(71) Applicant: Hemant V. Virkar, Gaithersburg, MD (US)

(72) Inventors: Hemant V. Virkar, Darnestown, MD (US); Thomas McCartan, Westminster, MD (US); Stacy Carroll, Clarksburg, MD (US); Matthew Cline, Pittsburgh, PA (US); Richard Gadbois, Gloucester, MA (US)

(73) Assignee: DIGITAL INFUZION, INC., Gaithersburg, MD (US)

( * ) Notice: Subject to any disclaimer, the term of this patent is extended or adjusted under 35 U.S.C. 154(b) by 231 days.

(21) Appl. No.: 16/193,990

(22) Filed: Nov. 16, 2018

(65) Prior Publication Data

US 2019/0156927 A1 May 23, 2019

Related U.S. Application Data

(60) Provisional application No. 62/587,834, filed on Nov. 17, 2017.

(51) Int. Cl.
*H04L 29/08* (2006.01)
*G16H 15/00* (2018.01)
(Continued)

(52) U.S. Cl.
CPC .............. *G16H 15/00* (2018.01); *G06F 16/21* (2019.01); *G06F 16/248* (2019.01); *G16H 10/20* (2018.01); *G16H 10/60* (2018.01)

(58) Field of Classification Search
CPC ........ G16H 10/60; G16H 20/17; G16H 15/00;
G16H 50/20; G16H 20/13; G16H 40/40;
G16H 40/63; G16H 50/30; G16H 50/50;
G16H 70/20; G16H 30/20; G06Q
30/0643; G06Q 30/0631; G06F 19/3468;
G06F 19/325; G06F 3/0488; G06F 19/00;
G06F 19/326; G06F 19/3462; G06F 16/2457;
(Continued)

(56) References Cited

U.S. PATENT DOCUMENTS

| 2016/0277374 A1* | 9/2016 | Reid ................... H04L 63/101 |
| 2017/0235466 A1* | 8/2017 | Tanwir ................. G06F 3/0481 |
| | | 715/738 |
| 2019/0096526 A1* | 3/2019 | Hirsch .................. G16H 50/70 |

* cited by examiner

*Primary Examiner* — Maroun P Kanaan
(74) *Attorney, Agent, or Firm* — Arent Fox LLP

(57) ABSTRACT

The disclosure relates to a computer system for managing medical research data. The computer system may include a network interface connecting the computer system a plurality of data providers. The computer system may include a plurality of data adaptors, each data adaptor configured to communicate with one or more of the data providers to obtain data in a respective data format. The computer system may include a data processor configured to control processing resources based on a volume of data obtained from the plurality of data providers. The computer system may include a plurality of data converters executed by the processing resources, each data converter configured to convert the obtained data from a corresponding data adaptor in the respective data format to a common data format including first metadata based on the obtained data. The computer system may include a data repository for storing data in the common data format.

19 Claims, 11 Drawing Sheets

(51) Int. Cl.
*G16H 10/60* (2018.01)
*G06F 16/21* (2019.01)
*G06F 16/248* (2019.01)
*G16H 10/20* (2018.01)

(58) Field of Classification Search
CPC ............ G06F 16/24578; G06F 16/248; G06F 16/3323; G06F 21/6245; G06F 16/21; G06F 16/27; G06F 21/602; G06F 11/2094; G06F 21/53; G06F 21/6227; G06F 21/6254; G06F 21/64
See application file for complete search history.

SYSTEMS AND METHODS FOR MANAGING CLINICAL RESEARCH

CROSS-REFERENCE TO RELATED APPLICATIONS

This application claims the benefit of U.S. Provisional Application Ser. No. 62/587,834 entitled "SYSTEMS AND METHODS FOR MANAGING CLINICAL RESEARCH" and filed on Nov. 17, 2017, which is expressly incorporated by reference herein in its entirety.

INTRODUCTION

The present disclosure generally relates to computer systems and methods for managing clinical research involving medical patients.

BACKGROUND

Medical research is typically organized into studies that track various groups of participants. As the ability to test and monitor patients increases, a large amount of data on each patient becomes available. Handling the large amounts of data for a medical study has become a problem in itself. The problem is further complicated by privacy concerns and regulations surrounding sensitive medical data.

Presently, there are a number of systems and associated formats used to collect medical data regarding study participants. Because the systems are not compatible with each other, not all data regarding a study participant may be available to researchers working with a particular data set from a system.

In view of the above, it can be appreciated that there are problems, shortcomings or disadvantages associated with clinical research, and that it would be desirable if improved systems to support medical research and manage research data were available.

SUMMARY

The following presents a simplified summary of one or more aspects of the invention in order to provide a basic understanding of such aspects. This summary is not an extensive overview of all contemplated aspects, and is intended to neither identify key or critical elements of all aspects nor delineate the scope of any or all aspects. Its purpose is to present some concepts of one or more aspects in a simplified form as a prelude to the more detailed description that is presented later.

In one aspect, the disclosure provides a computer system for managing medical research data. The computer system may include a network interface connecting the computer system a plurality of data providers. The computer system may include a plurality of data adaptors, each data adaptor configured to communicate with one or more of the data providers to obtain data in a respective data format. The computer system may include a data processor configured to control processing resources based on a volume of data obtained from the plurality of data providers. The computer system may include a plurality of data converters executed by the processing resources, each data converter configured to convert the obtained data from a corresponding data adaptor in the respective data format to a common data format including metadata based on the obtained data. The computer system may include a data repository for storing data in the common data format.

In another aspect, the disclosure provides a method of controlling access to medical research data. The method may include tagging each field of records with a metadata tag. The method may include assigning a role to each user of a research management system. The method may include receiving a request to display information from the records to a user. The method may include for each field to be displayed, determining whether to display, hide, or mask contents of the field based on the role of the user.

These and other aspects of the invention will become more fully understood upon a review of the detailed description, which follows.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

A research management system provides various research study participants with information regarding the research study based on each participant's respective role within the research study. A data ingest system collects various forms of data from different data sources and compiles the raw data into a document repository where the data is labelled with metadata. The raw data is then processed using the metadata via a data pipeline into a data warehouse, where the data may be analyzed. A management portal controls access to the data warehouse and presents different views of the data to the participants based on their respective roles. The management portal protects private information by only providing access to the roles that need the data. The research management system also tracks transaction data regarding participant roles and generates an audit trail to determine how data has been modified.

Figure 1:
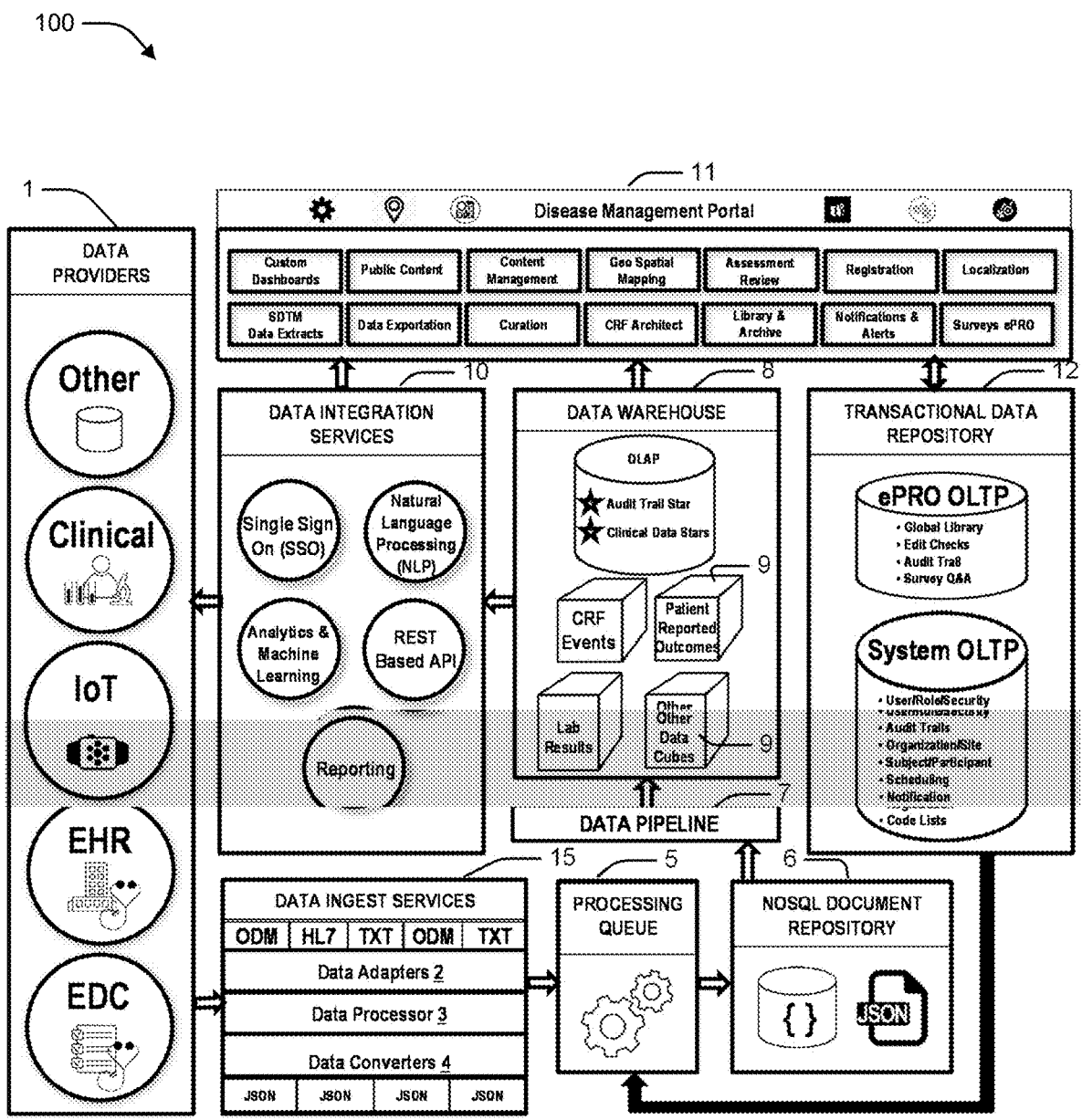
FIG. 1 is schematic diagram showing an overview of a research management system, according to an aspect of the disclosure.

FIG. 1 illustrates a high-level conceptual architecture of a research management system 100. The research management system 100 generally includes data providers 1, data ingest services 15, a data processing queue 5, a document repository 6, a data pipeline 7, a data warehouse 8, a transactional data repository 12, data integration services 10, and a management portal 11.

The data providers 1 may include independent sources of data that may be integrated into the research management system 100. The data providers 1 may use a variety of data schemas and transmission mechanisms, follow different schedules of data interchange, and originate from many different external and internal providers. The research management system 100 may process standard based data formats, such as Clinical Data Interchange Standards Consortium (CDISC) Operational Data Model (ODM) and HL7 messages, but the research management system 100 is designed to be flexible enough to handle other formats, such as CSV, XML, Ascii, etc. The research management system 100 includes a robust, scalable and reliable architecture that can accurately process, transform and integrate these external data sources using a reliable, consistent approach. The architecture supports existing data sources, such as Medidata Rave electronic data capture (EDC). Additionally, the research management system 100 may use a modular architecture that allows future data sources to be added with minimal intervention or modification to the overall design of the research management system 100.

The data ingest services 15 provide an interface between the data providers 1 and the research management system 100. The data ingest services 15 may include data adaptors 2, a data processor 3, and data converters 4. A first layer of the data ingest services 15 is a thin, modular layer of data adapters 2 which can be configured to work with a variety of different data providers 1 in a reliable format. For example, the research management system 100 may include a data adaptor for each data type of the data providers 1. A data adaptor 2 may be a software module that communicates with a particular data source. For example, a data adaptor 2 may provide an API that allows a data provider 1 to provide data to the research management system 100. The data adaptor 2 may also execute protocols for retrieving data from a data provider 1. Each data adapter 2 may obtain a specific data type using an interchange format in a reliable, consistent method. This common mechanism may be extended for each data provider 1 that uses a specific data type (e.g., ODM). Additional data adapters may be added as new data types are transmitted by data providers 1. Format examples that are represented by existing external providers include ODM, HL7, CSV, Excel, TXT, Comma Separated, SAS, JavaScript Object Notation (JSON) and HTML. Each data adaptor 2 may include a specific interchange mechanisms for the respective data type that can also be categorized (e.g., FTP, Web Services, RSS, Web Site Driven, etc.).

By utilizing the data adapter framework, a change in provider input data may not affect the research management system 100 downstream from the data adaptors 2 (e.g., because the new provider input may be adapted to a common format using a different data adaptor 2). The research management system 100 may respond quickly to changing data input needs by modifying or changing the data adaptor 2 assigned to the changed data provider 1. Additionally, data adapters 2 can be re-used and re-purposed for any of the external data providers 1 (both current and future) by assigning an existing data adapter to the external data provider. For example, if a new data provider 1 uses the same format and interchange mechanism as an existing data provider, the same data adaptor 2 may be assigned to the new data provider 1. As another example, if a data provider 1 changes to a format standardized on ODM interchange, such as BioClinca, and the data provider 1 was previously using Medidata ODM, the research management system 100 may already have a common data adapter 2 (e.g. used by a different data provider 1) that can process ODM files. The existing data adapter 2 may be connected to the changed data provider 1 via any of the standard interchange mechanisms, such as file transfer protocol (FTP) or Web Services.

Some data providers 1 may use manual methods, such as providing physical files, or emails directly to the research management system 100 for manually processing. In these circumstances, a data adapters 2 can be customized to process this data in a more automated fashion, such as a File Upload Utility through a web portal. Another method may be a file watcher service, where the data providers 1 can place a file on a known location such as a directory or FTP site. One or more data adaptors 2 may be configured to access the known location and retrieve the file for processing.

The data processor 3 may be a scalable processing module to process the data once it has been received by the data adapters 2. In an aspect, the data processor 3 may be implemented using a cloud processing service that allows expansion of processing resources to meet processing demand. For example, the data processor 3 may be able to expand data processing resources when receiving a bulk delivery of records or integrating a new data provider 1. The data processor 3 may process data from all of the current and future data providers 1 in an efficient manner. The data processor 3 may provide common services to support robust data processing (e.g., scheduling, auditing, logging, exception handling, notifications and monitoring). The data processor 3 may consistently process the data from the data providers 1 before sending the transaction records to the data converter 4 (e.g., a JSON document conversion processor). Since interchange mechanism schedules vary, the data processor 3 may provide configuration services to the data adapters 2 so that each external data provider 1 can establish an optimal schedule for providing data to the research management system 100. By using a common data processor 3 that handles and logs all processing for all data adapters 2, the research management system 100 may generate a detailed audit log of all transactions occurring within the system.

The data processor 3 may include an operations dashboard. The operations dashboard may be a single data ingest monitoring interface that may display to one or more permissioned operators all activities, or a subset of activities, that occur within the research management system 100 in real time. The data processor 3 may run analytics services using a cloud-based service (e.g., Stream Analytics) to automatically update the operations dashboard with relevant data. The data processor 3 may also provide dashboard elements, using Power BI, for monitoring the amount of data processed, connections being made, exceptions, alerts, and future data pulls.

Figure 2:
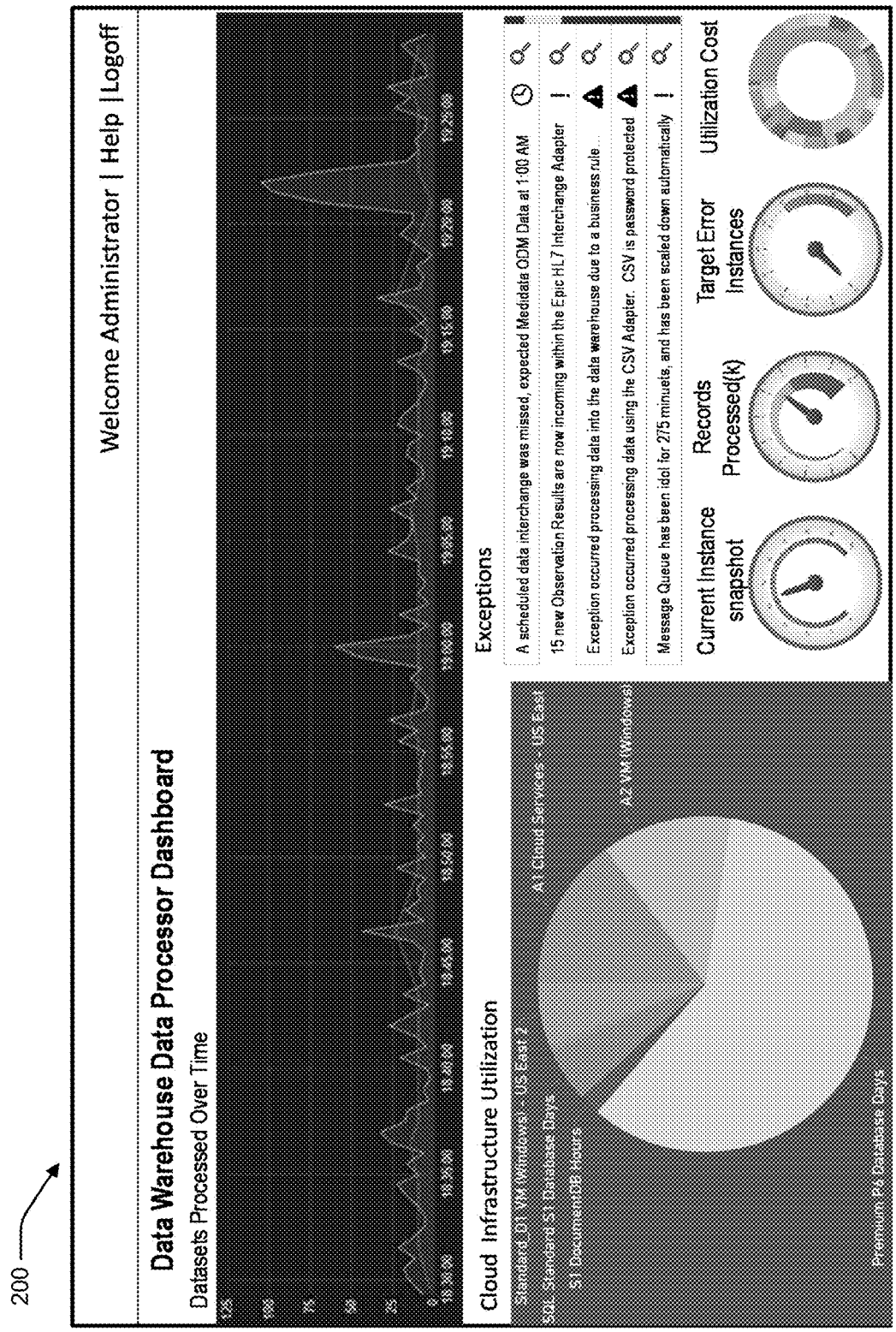
FIG. 2 is an example user interface of a data processor dashboard, according to an aspect of the disclosure.

FIG. 2 is an example of an operations dashboard 200 that is securely exposed to a permissioned operator of the research management system 100. The data processor 3 may track a tremendous amount of data (e.g., 1 TB/hour). Due to the volume of data, the research management system 100 stores incoming data in a document repository 6. For example, the document repository 6 may be a cloud-based NOSQL table storage service. Table storage provides key/value storage through a schema-less design, which makes it easy to adapt to the structure of the incoming data. Accordingly, table storage may be a relatively inexpensive data storage mechanism for storing audit, logging, exception and processing information. The data stored in table storage can be efficiently queried and exposed to analytics tools (e.g., Tableau, Power BI, and Hadoop) for high-end analytics on data processing and operational activities. Accordingly, the data processor 3 layer of the architecture will be able to consistently process the data and hand it off to the data converter 4.

In an aspect, the data processor 3 may not be responsible for executing business rules on the incoming data. Instead, business rules may be applied by the data pipeline 7. The main responsibility of the data processor 3 is to accept in-coming data, in whatever format, and properly convert the incoming data to JSON for storage in the document repository 6.

The data converters 4 may be lightweight interfaces that can take a specific data format (e.g., ODM, HL7, CSV or TXT) and convert each transaction record received from the data providers 1 into a standard JSON document. Since external data providers 1 may provide data in different categories of data, the data converters 4 may use JSON as a standard data format. For example, JSON is lightweight, self-describing and built for easy integration into other data formats and applications. A person skilled in the art should appreciate, however, that a different standard data format may be selected. In an aspect, the research management system 100 platform architecture is designed upon the CDISC ODM Standard. Each JSON document may be created using the ODM requirements and be formatted appropriately to meet the specification outlined by CDISC. However, instead of being an XML document, the ODM JSON document may be implemented in JSON. Once the data converters 4 create the appropriate ODM JSON document, the data converter 4 may create a Service Bus Message and place the ODM JSON Document in the data processing queue 5 where the ODM JSON Document can be picked up and stored in the NoSQL document repository 6.

As new external data providers 1 utilize the research management system 100, a simple modification to configure a new data adapter 2 and data converter 4 may be implemented. Once the data adaptor 2 and data converter 4 are changed or updated, the data may be stored directly into the document repository 6. The modification of the data adaptor 2 and/or data converter 4 can happen on the fly and with little or no changes to the underlying processes, procedures or data storage services.

The actual source data stream (e.g., JSON ODM documents) may be kept within the document repository 6 in blob storage. A blob may be unstructured raw data such as text files, images, binary data, video, etc. A blob may also include metadata that describes the blob. For example, the metadata may describe the source of the blob, the reception time of the blob, and the content type of the blob. The blob metadata may be used for archive and auditing purposes. The use of schema-less blob storage may enable the research management system 100 to have a storage mechanism that can handle current and future needs without modifications to the underlying data structures and services.

JSON data may be stored as arrays in records, which can be read into object-oriented languages. As such, using JSON data in Web-based processing and transformation languages (e.g., Perl, Ruby, JavaScript, and .NET) is very easy and efficient. JSON's flexibility also allows the data ingest services 15 to incrementally process the incoming data without depending upon data sources to resend everything when the source data structure changes.

In addition to providing the transactional data, each ODM JSON document may contain a complete set of metadata that is specific to the data interchange structure and source. The metadata provides details of the transaction record, data processed and source of the transaction data as it was received. By including the metadata within each document, each document can be processed by the research management system 100 independently at any time, in any order, without the need for any additional data. The metadata elements stored within these transactional ODM JSON documents allow external data source schemas to change over time, while maintaining an accurate historical snapshot of the source record with the associated version of the metadata to process that record. The associated version of the metadata may allow re-processing data in a consistent approach. For example, historical records may be processed with their unique metadata, while future transactional records where the schema has changed may be independently processed with their metadata schema.

The combination of the data providers 1 and the data ingest services 15 enables seamless data ingestion, regardless of the input type. Such an ingestion process allows for maintaining flexibility, handling changed data elements, and accommodating additional transaction records with little or no changes made to the processing logic. The data providers 1 and the data ingest services 15 allow all input data to be processed into the document repository 6, where the documents may be stored in a standard ODM JSON format for further ETL processing.

The data processing queue 5 may be a dynamic queue provider that listens for messages that need to be inserted into the document repository 6. The data processing queue 5 may be implemented using either on premise infrastructure or cloud-based messaging services. Each message in the data processing queue 5 may be a pointer to an ODM JSON document to be stored in the document repository 6. Ultimately, the operational data being logged in the data processing queue 5 can be accessed through the management portal 11 for viewing messages in the data processing queue 5, errors in the queue, and processing throughput.

In an aspect, there may be a processing cost advantage of having the data processing queue 5 implemented in the cloud, because a cloud implementation allows the data to be processed at different times and schedules and only uses processing resources when they are needed. The data processing queue 5 may scale up processing resources according to the load and scale down when processing load is diminished. The variable processing resource may be important when processing data for the first time, re-processing data, or processing data during peak load times. Furthermore, a message queue architecture provides services where every transaction may be audited and logged in the same repository as the data processor 3.

The document repository 6 may be a data storage that contains all of the transactional data from the data providers 1, along with their related metadata and audit data (e.g., date received, date processed, data source and transactional information, etc.). The document repository 6 may contain a standardized and structured snapshot of the data that represents the source transactions from the data providers 1.

The processing queue 5 may process data in the blob storage into the document repository 6. For example, the processing queue 5 may parse the blobs into usable data structures, for example, based on JSON tags. Additionally, JSON is the standard data format for document repositories, which allows the document repository 6 to automatically provide query-ready indexes.

The document repository 6 can be scaled up or down at any time and on-demand to reduce storage costs. Scaling may be needed for when data needs to be archived, backed up, or re-processed. By utilizing a scalable set of infrastructure, storage can be optimized in an efficient and dynamic way.

Document repository data may contain a complete set of transactional data—along with detailed metadata—regarding the data's source. Once the transactional data and the metadata data is in the document repository 6, the data can be used by the management portal 11 at any time and for any purpose. The document repository 6 may be implemented by a cloud provider that stores the data in geo-redundant locations, which may protect against natural disasters or unexpected failures.

Since the document repository 6 may store detailed transactional data, it is unnecessary to re-process data from the external data providers 1 in an event that the data warehouse 8 needs to be updated or rebuilt. The data warehouse 8 may use data pipelines 7 to query the document repository 6 for only the changed, added, or removed data, which may be used to update the data warehouse 8 with the relevant information in an incremental fashion.

The document repository 6 may be implemented using standard NoSQL services such as Mongo DB or Azure Document DB, hosted in a partner cloud provider such as Microsoft Azure. NoSQL storage of unstructured, document-centric data can be scaled up or down on an as-needed basis by distributing the database across multiple hosts as the load increases. The data can be queried in a SQL-like language structure and exposed via a REST based API, and then queried data can be directly integrated into AJAX Services, Web APIs, Solr Indexes, Power BI, Angular front ends, and numerous other reporting, UI visualization tools and analytics services.

Figure 3:
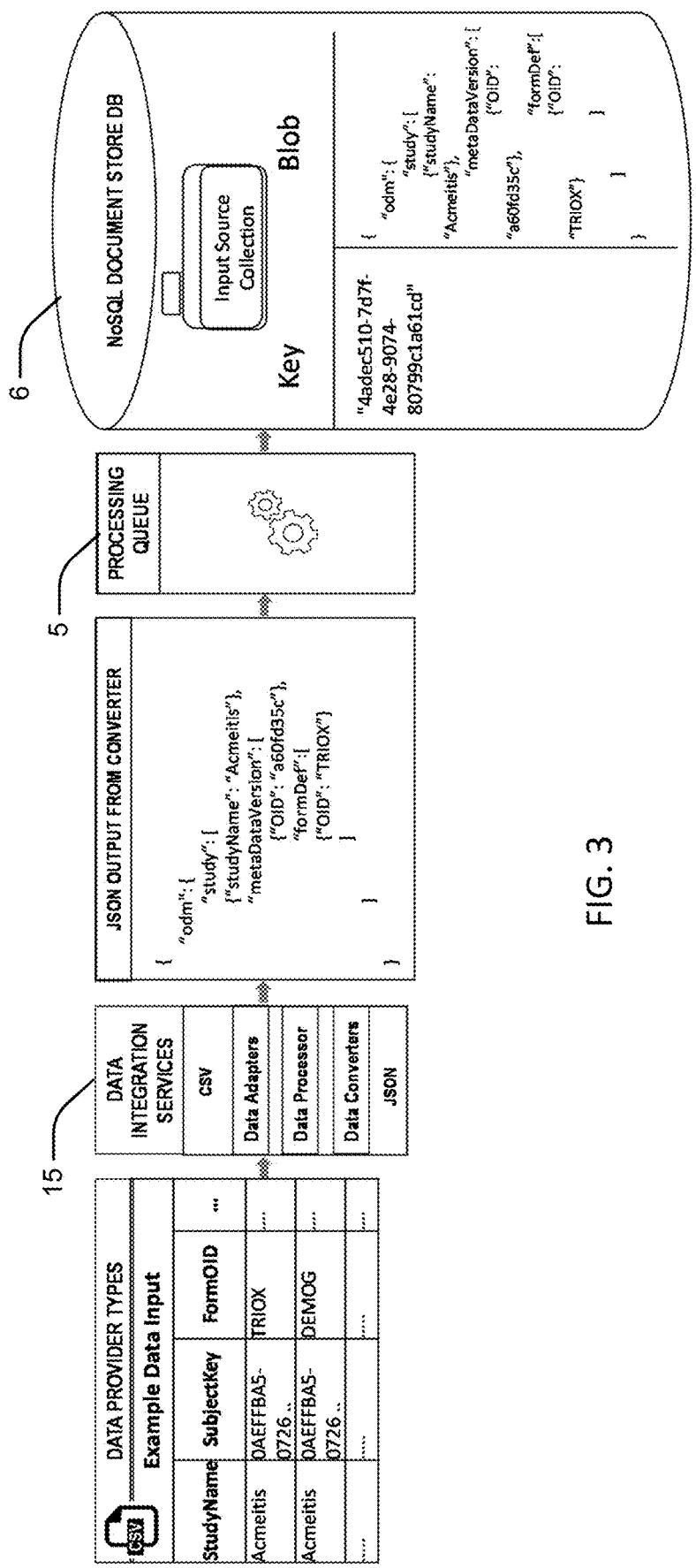
FIG. 3 is a schematic diagram of data structures for ingesting data into the research management system, according to an aspect of the disclosure.

FIG. 3 illustrates an example of processing data from data provider 1 into the document repository 6. For example, the data provider 1 may provide data in a CSV format. The data integration services may convert the data provider data to JSON, and then store the converted data in the document repository 6. In particular, FIG. 3 depicts how a JSON transaction document may be stored as a "Blob" within the document repository 6.

Data pipelines 7 may be responsible for moving data, validating data, and processing data analysis rules. In this case, the data pipelines 7 may incrementally publish the raw transactional data from the document repository 6 into the data warehouse 8. Data pipelines 7 can be grouped together into a data factory to efficiently and consistently transform and publish the data so that the transaction data can be consumed and stored into the online analytic processing server (OLAP) database of the data warehouse 8. A data analysis rule may be any rule, process, or formula that is used to extract or transform data from the common format. In an aspect, data analysis rules may include business rules. Examples of data analysis rules implemented by the data pipeline 7 may include "BMI calculation, age specification (in months if age<2 yr, in years if age >+2 years)." For instance, a data pipeline 7 may extract data from a medical record identified as an age in years and convert the age to months if the age is less than two years before using the age in a BMI calculation formula along with other extracted fields (e.g., height and weight).

The combination of the document repository 6 and the data pipeline 7 provides a consistent approach to performing Extract, Transform and Load (ETL). The ETL tools, technologies and processes will be constant, because the source of the transactions have been transformed from unstandardized, disparate formats to a single ODM JSON repository of individual records with detailed metadata. Processing resources that work within this layer will always have access to the source structure and destination of the data, and the processing resources do not have to adapt to changing formats to process existing data, new data, or changed data.

The data warehouse 8 may be the final destination for the processed data. The data may be transformed and inserted into logical relational structures, based on a common domain model. Other applications may then consume the transformed data for dashboards, reports, and analytics. The data warehouse 8 may contain a structured query language (SQL) server and a multi-dimensional, online analytic processing server (OLAP). The SQL server may contain the relational data that was published from the data pipelines 7, while the OLAP server may perform the following operations: Roll-up, Drill-down, Slice and Dice, and Pivot.

All the clinical and metrics data may be stored at the most granular level. While some "out of the box" pre-determined aggregations/consolidations are available, most custom requirements are easily catered using data cubes.

The data warehouse 8 may be a dynamic data housing solution using a dimensional model for reporting and analytics. Data from various data providers 1 flow into the data warehouse 8, creating a centralized structure for accessing study data. The data warehouse 8 acts as the source to display all data analytics, reports, and data insights of all information relevant to the logged in user. This information is stored in a preprocessed repository, to support high throughput analytics, and is typically updated to end users within a 15-minute window.

In an aspect, the data warehouse 8 may include OLAP data cubes 9. Output from the OLAP processing are the OLAP data cubes 9, which may contain preprocessed multidimensional views of the contained data. OLAP data cubes 9 may provide business domain services that can be exposed to external/internal data consumers such as study participants, managers, and analysts. The OLAP data cubes 9 may be stored in a flattened schema that contains pre-calculated measures that are generated from the complex data warehouse transactional data. Data cubes 9 can be directly integrated into third party reporting tools, web applications, and data services, reducing the need to join together multiple tables and conduct on-demand calculated services.

For example, data cubes 9 may include cubes for audit metrics that will allow for reporting on different audit actions that are performed. Quantitative metrics like subject count by site/study, forms entered by site, etc. and qualitative metrics like open queries by subject/site, non-conformant metrics, etc. may be delivered via pre designed cubes. Additional custom audit metrics can be provisioned as needed using custom designed cubes.

As another example, data cubes 9 may include cubes such as laboratory test result, clinical assessment results, etc. that will provide data on a particular set of clinical forms. Data sets that may be of interest to a particular party or for a particular study may be delivered using custom built data cubes 9. For example, custom data cubes may track data over time to establish wellness patterns/trends based on patient reported outcomes. Example reports may include "Effect of Treatment on Laboratory Test Results" or "Disease progression based on patient reported outcomes."

Data integration services 10 may include of a set of components that provide specialized activities on the data and for the consumers. Ultimately, these services enable the management portal 11 to function as a "one stop shop" for all data.

The data integration services 10 may include a web-API interface. The web API Interface level may be built incrementally on top of the data warehouse to expose important data to customers. This layer of the integration services may be used mostly by internal applications and services. By creating a standardized REST-based Web API layer to the backend data warehouse and OLAP Data Cubes, the web API interface level may provide applications and services with a master set of data that can be relied upon as the source of record.

The data integration services 10 may include one or more reporting modules. For example, the reporting modules may be based on enterprise level BI tooling. The research management system 100 may be standardized on PowerBI, because this tool can directly integrate with any of the data repositories (e.g., the data warehouse, data cubes, or the document repository). The reporting modules can be exposed to both the portal 11 as well as other external applications for ad-hoc reporting needs.

The data integration services 10 may include analytics module. In alignment with the goal of research institutes to become an increasingly data-driven, the addition of high-end analytics (e.g., trends, predictive analytics, and machine learning) improves the ability of research management system 100 to discern actionable intelligence from data. The data repositories in the research management system can be used with services such as Azure ML, Hadoop, Spark, R and other data analytics services.

The data integration services 10 may include a natural language processing module. The research management system 100 may facilitate natural language queries of repository data. Customers may ask questions and receive immediate results from the research management system that are insightful. Such questions may be, "What were the number of patients in Missouri with no prior symptoms of the disease?", or "What was the percent change in health indicators for populations when treatment began?"

The data integration services 10 may include a single sign-on (SSO) module. Since the research management system 100 contains the ability to integrate with any external data provider, the research management system 100 may also seamlessly interact with these systems. The research management system may be standardized upon the SAML Security Protocol for providing single sign on services to and from the disparate platforms. This enables users of the research management system 100 to securely sign into the portal 11 and then seamlessly access external systems that are integrated with the research management system 100.

The data integration services 10 may include an eLearning module. The research management system 100 may include an eLearning management module that may deploy, manage, and launch eLearning courses. The eLearning management module may include a deployment dashboard that allows study personnel to add and update courses, associate courses with studies and roles, and set course attributes. The eLearning management module may include a management dashboard that allows study personnel to manage courses for all users, track compliance, course overrides, and progress of eLearning courses for each individual user. The eLearning management module may include individual eLearning dashboards for each user to track eLearning progress and launch courses.

The management portal 11 provides a web-based front-end for content, analytics, reporting, and patient-facing Electronic Patient-Reported Outcome (ePRO) functionality. The portal 11 may be based on an open-source content management system called DNN. DNN provides the ability for non-technical users to create and update public content on the site, such as disease information and patient newsletters.

The portal 11 may use the AngularJS framework to provide high performance and cutting-edge interactivity. The Angular application may connect to a web API to retrieve and process data. The application may be modular and customizable, allowing each customer the ability to choose the data they collect and display. The portal 11 may use the Solr search engine to provide near-real-time search for patients, organizations/sites, health care providers, and ePRO data. Solr also provides faceted search capabilities that allow users to build powerful search queries using an intuitive, familiar UI. Additionally, the portal 11 may host PowerBI reports for deep analytics.

The portal 11 may include a user interface built using the Bootstrap UI framework. This open-source framework provides a responsive design that allows the portal 11 to display correctly on multiple screen sizes, from mobile phones to widescreen desktop monitors. The Bootstrap framework allows for deep customization, allowing the portal to be adapted to each customer's unique branding and visual design.

The transactional data repository 12 may be responsible for storing all ePRO and research management system relational information to support the management portal 11. The transactional data repository 12 may store all case report form (CRF) definitions, transactional metadata, libraries, organizations, sites, security, participant, registration and profile information. The information may be used for supporting the management portal 11 and ePRO management systems. Changes, updates, and soft delete transactions to ePRO data may be sent back to the data processing queue 5, and then used to update the data warehouse 8 and data cubes 9 and propagated to external users.

The data integration services 10 includes a self-service reporting tool that securely connects to the data warehouse 8, allowing users to build reports and data visualizations for their research studies. The research management system 100 may include a standard set of reports that can be configured through the self-service reporting feature. Users of the research management system 100 may be assigned user roles based on their respective role in a research study. The research management system 100 may allow users to generate and deploy different reports based on the user role. With access to the study metadata, a customer can design and build his or her own reports based on dynamic study data. Using the report designer to access the data warehouse 8, the customer can then publish role based reports to all users, to any dashboard, and to a variety of mediums (Web and Mobile). The reporting tool provides customers with full control over what data they want to include, where they want to deploy the report, and to whom they want to deploy the report.

The management portal 11 may include dashboards and workspaces that are controlled through role based security. For example, the following dashboards and workspaces may be pre-generated for any customer. A site dashboard may be used by physicians to view of all of their patients at all their sites. A data management dashboard may be used by Data Managers to view and manage all incoming data that is integrated within the research management system 100. An ePRO dashboard may be used by managers to view and control patients' surveys. An administration module may be used to create sites, users, notifications, organizations, etc. A participant workspace may be a specific workspace filtered on a patient's unique criteria. Data from reports may be trimmed based on the user accessing the report. Additionally, reports may filtered based on role. The research management system 100 also has the capabilities to mask certain data elements, using data-tagging, where information can be shown clearly to some roles, but masked to others. This allows customers to control who can see what, as it relates to protected health information (PHI).

A user role of a reports designer may create additional reports with the self-service reporting tool. The reports can be imported into the research management system 100. Using the reports manager workspace, reports and data visualizations created with the self-service reporting tool can be selectively deployed to various role based workspaces and dashboards, such as the site workspace, participant dashboard or the reports workspace.

The self-service reporting tool may allow a user role of study manager to deploy reports to the participant dashboard so that participants can get more information about their study. For example, the study manager may choose the participant heat map report. The study manager may deploy the report to the participant dashboard. The reports deployment summary shows the heat map report has been deployed to the participant dashboard.

A user role of a primary investigator may deploy reports to the site dashboard so physicians can get more information about participants at their study site. The primary investigator may choose the patient clinical summary report to deploy the report to both site and participant dashboards. The reports deployment summary shows the patient clinical summary report has been deployed to the participant dashboard and the site dashboard.

The reports display module is a container for self-service created reports, displaying multiple reports and data visualizations for the entire study, for a study site, or for individual participants, all created with the self-service report creation toolset. The reports display module can be added to workspaces and dashboards.

A user role of a participant may view reports on a participant dashboard. The participant may log into participant Dashboard, and navigate to a reports page. Reports deployed to a participant's dashboard are on display in the reports page.

A user role of a physician may view reports for all participants at a study site, and for individual participants at the study site. The reports are displayed in the site dashboard reports viewer. If the logged in physician selects a study site, the report shown will be a roll up of all participants at that study site. If the physician selects a participant, the report shown will be for that individual participant. Further, if multiple reports have been deployed to any given dashboard, the user can select each report using the tabs at the bottom of the reports viewer.

In an aspect, a study may be associated with one or more regions. The regions are unique to the study. A region role may be assigned to study personnel to facilitate management of a region. Regions may be associated with study sites, personnel with a region role, and other regions. When personnel are associated with any given region, they will have access to all study sites associated with the same region. The common region allows the personnel access to the study sites. In an aspect, a region may have zero or more child regions to further sub-divide the study. Personnel associated with a parent region are also associated with the child regions. Personnel may have multiple region roles.

The research management system 100 may use an advanced multifactor authentication architecture based on Active Directory. Each unique customer may be assigned their own dedicated Active Directory that is linked to the research management system. The Active Directory gives the customer control over user roles of users associated with the research studies of the customer. Users of the platform create and maintain their own user accounts and associated passwords through multi-factor authentication. Login screens, change passwords and all other associated security dialogs are customizable and brand-able. Default multi-factor authentication may utilize email and phone number for validating a unique user.

For example, a new user may set up an account to log in to a study. The new user may require approval from a study manager user role. Once approved by the study manager, users are sent an email asking them to create their account. The invitation email provides them with a unique invitation code/URL. The user uses the URL with unique code and is required to go through multi-factor authentication to create their account. The user is required to authenticate via phone and the user is required to authenticate via email. Once fully authenticated, the user may create a password and log in to the research management system 100.

Figure 6:
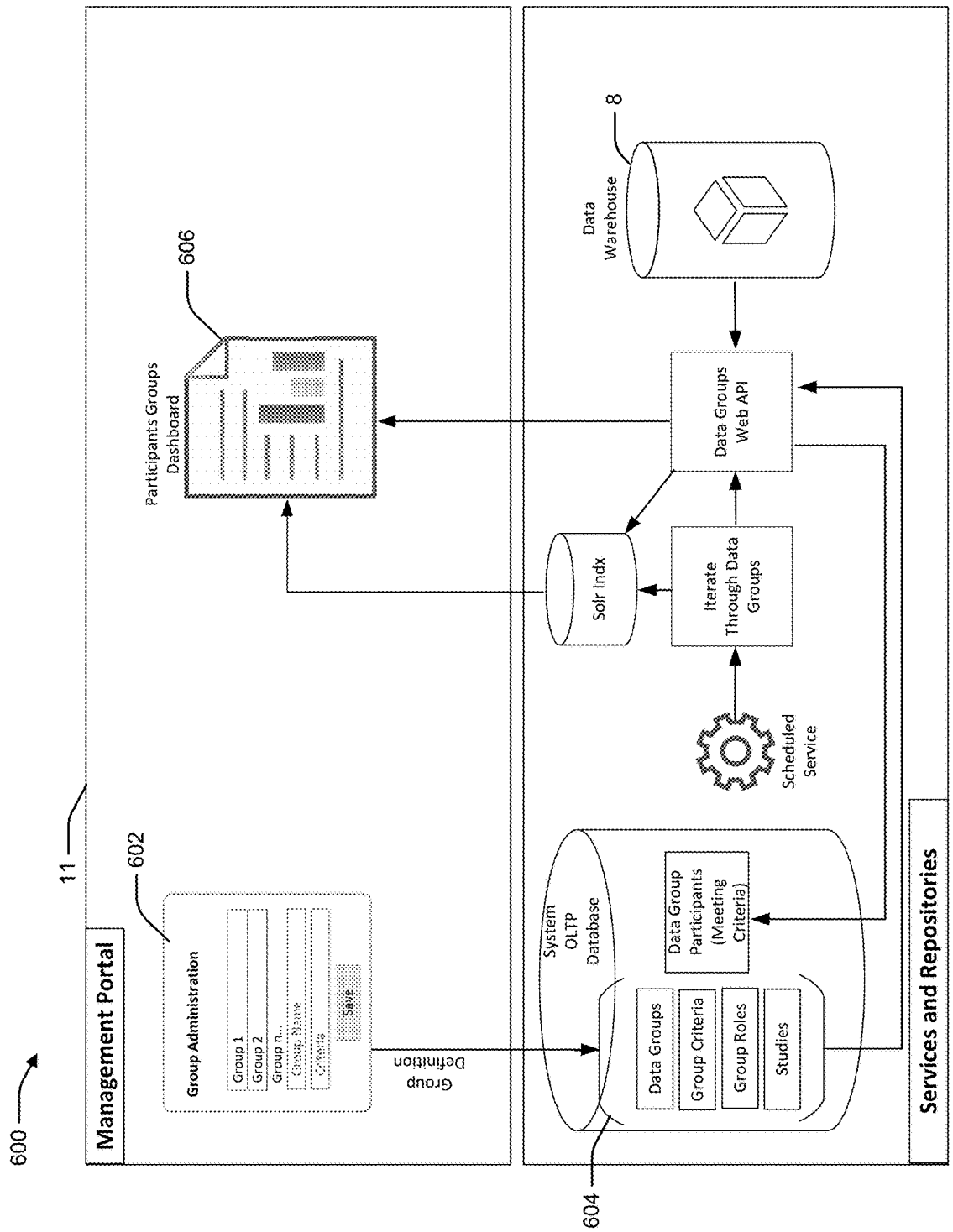
FIG. 6 is a schematic diagram of an example architecture for controlling access to data using participant groups, according to an aspect of the disclosure.

Study personnel with permissions can create groupings of participants based on metadata of subjects using common metadata across participants. FIG. 6 illustrates an example architecture 600 for managing participant groups. The participant groups may be managed using the management portal 11. Authorized study personnel may assign a unique group of participants to user roles for easily accessing, analyzing, and managing groups of participants that have common attributes. Any given data group can have one or more studies, criteria, associated roles, and participants. A data group with multiple criteria referencing all associated studies will relate all participants matching that set of criteria, allowing users with access (by their role) to view the group.

For example, a study manager may create groups of participants based on common data and states using a group administration tool 602. For instance, a group may represent participants enrolled in ePRO to focus on only those participants that are enrolled. The study manager may create a group of all ePRO enrolled participants from all studies, all study sites. The study manager may choose all studies and participants with an ePRO status of enrolled. An "ePRO Enrolled Participants" group may be saved, and created. For example, a group definition 604 may be stored in the transactional data repository 12.

The participant groups dashboard workspace 606 utilizes participant groups to display any given selected set of participants. Similar to the site dashboard workspace, but instead of viewing participants by site, participants are displayed by group, allowing deep cross filtering of participants, across study sites, study data, location and demographic data. For example, for the above group of participants enrolled in ePRO, the study manager may navigate to the management workspace and select "ePRO Enrolled Participants". All participants enrolled in ePRO may be displayed. Participant info, questionnaires, and reports are shown for all and only those participants enrolled in ePRO.

Figure 4:
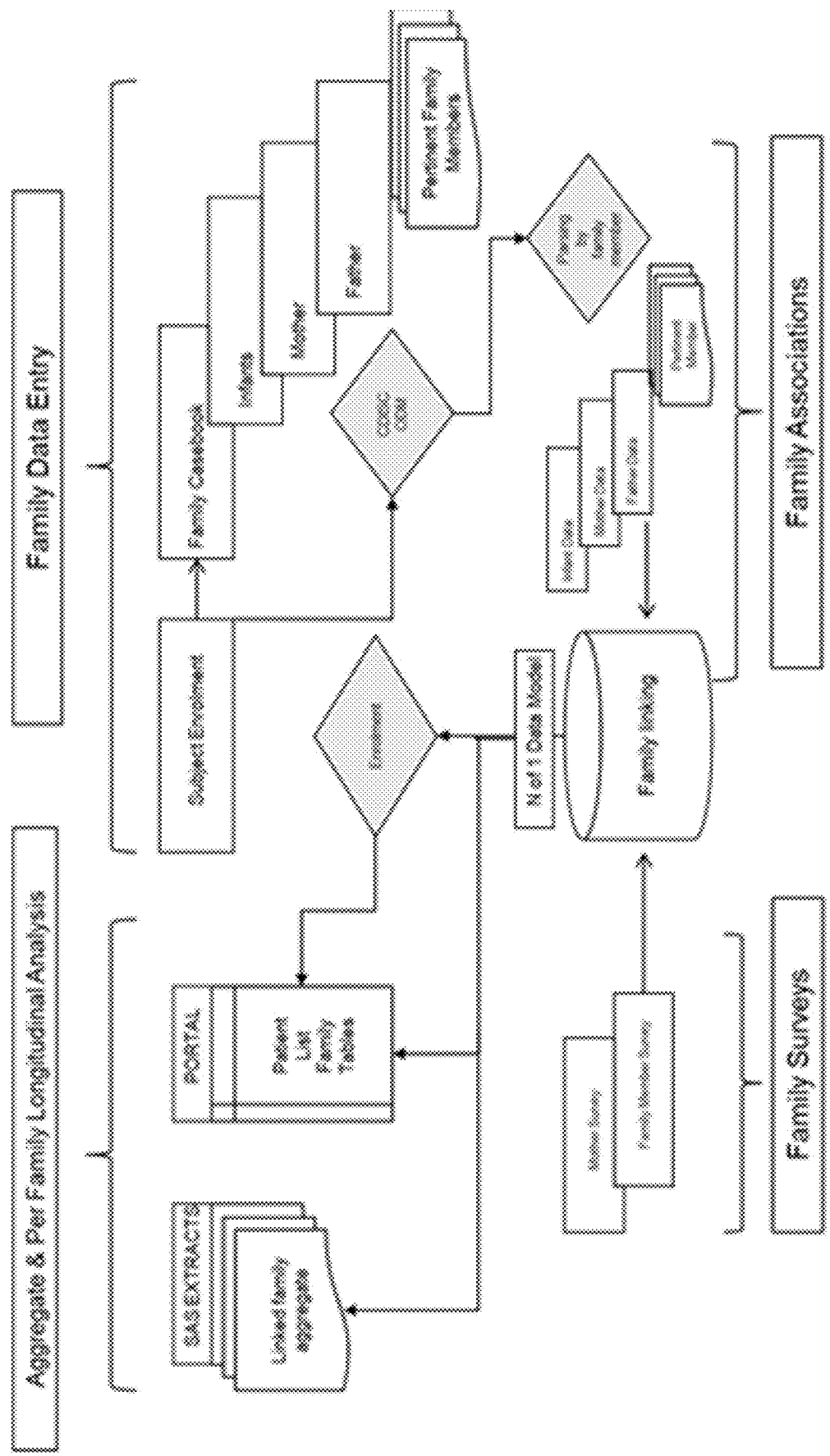
FIG. 4 is a schematic diagram for managing data using a familial model, according to an aspect of the disclosure.

In an aspect, participants may be organized based on family. FIG. 4 is a high level architecture and processing schema for supporting a familial model. The familial model may be used to support multiple users, who may use a single device. A family may include multiple patients (e.g., in cases of genetic disorders) as well as other members who may act as caregivers or delegates for the patients. The familial model may define roles and relationships among the family members. Data provided by a family member may be tagged such that the relationship to other family members can be analyzed. For example, a mother may be designated as a delegate for each child and permitted to fill out questionnaires for the children and the mother. The children may each be assigned to the family and enrolled in ePRO to allow the mother to proxy the questionnaires. If a father only needs to fill out questionnaires for himself, the father may be enrolled in ePRO but not assigned a delegate role. A grandparent with relevant laboratory results may be associated with the family, and data may be captured through EDC. A physician may be able to view all of the family information from the physician role. A nanny role may be assigned to a person who fills out questionnaires for many participants, and may be a delegate for each of the participants. A family wizard tool may be used by a study manager to add families and family members, and configure the family associations based on individual family structure and needs.

In an aspect, the research management system 100 may associate questionnaires with honorariums, which may be provided in the form of gift cards. When a questionnaire is completed, the participant becomes eligible to receive a gift card. The research management system 100 may include an honorarium management feature that allows study personnel to manage, send, and track gift cards across all participants in the study. The honorarium management feature may allow sending both eGift cards and physical gift cards. The honorarium management feature may allow a study manager to associate an honorarium with a questionnaire by selecting an amount, reason, and third party vendor for the honorarium. The status for the honorarium may be initially set as not eligible, and may be set to eligible when the participant completes the questionnaire. Study personnel managing the questionnaire may then manually or automatically award the honorarium based on the completed questionnaire. The honorarium management feature may send a processing request to a third party gift card provider and track the delivery status to the participant.

The research management system 100 may provide data security and privacy protection. For example, the research management system 100 may provide a full audit trail of ePRO questionnaires. The audit trail may be stored in the transactional data repository 12. Some items including protected health information (PHI) may be stored in a separate structure to support validation requirements. All updates to questionnaires are fully auditable based on the old value, new value, who made the change, when and why the change was made. The audit trail may be made available to assigned user roles to view the complete history of all changes done to every questionnaire form and field.

Figure 5:
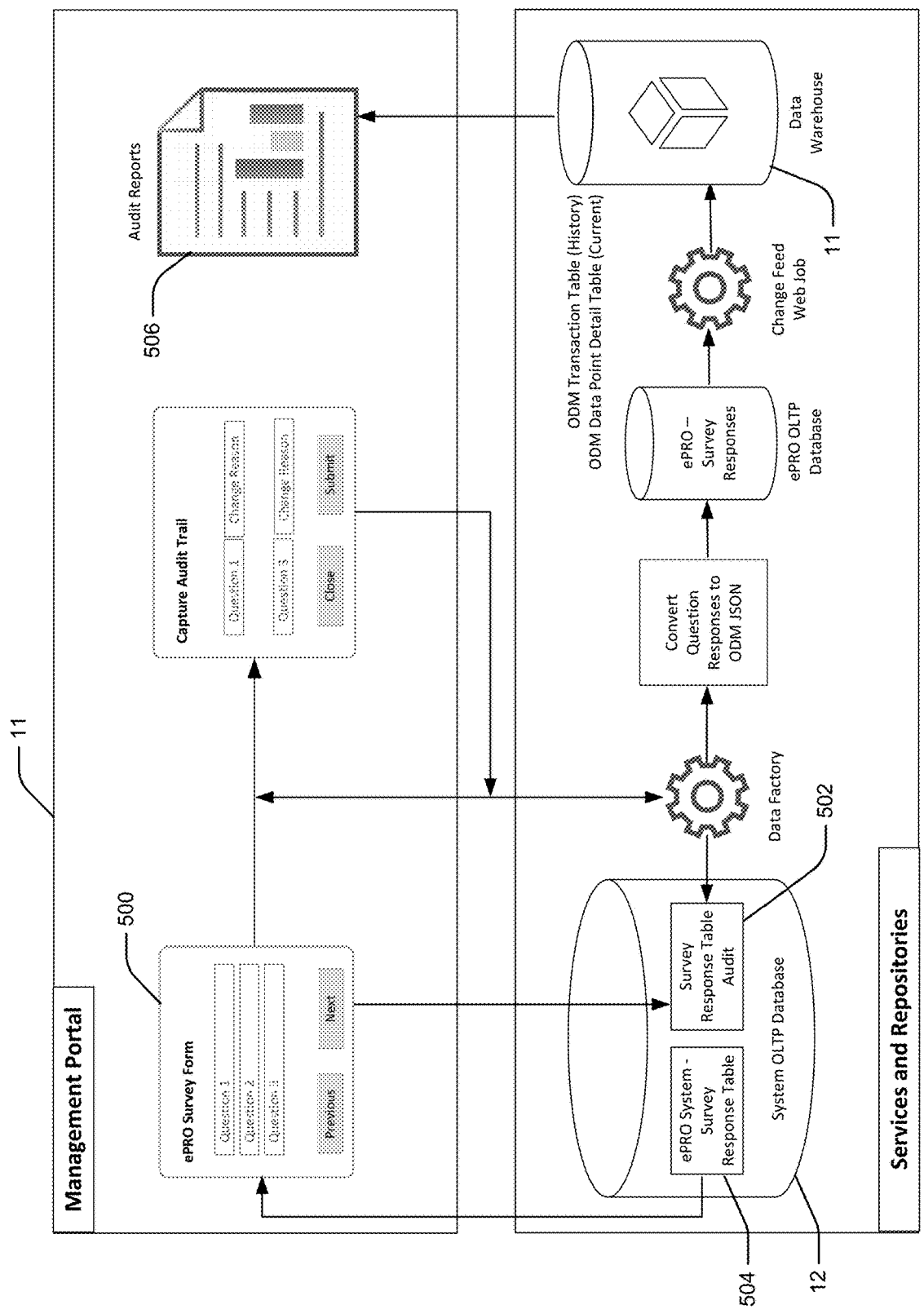
FIG. 5 is a schematic diagram of an example architecture for providing an audit trail of surveys, according to an aspect of the disclosure.

FIG. 5 illustrates example storage and processing of audit trails. For example, users may complete ePRO survey forms 500 through either an ObsRO vendor or an ePRO module in the management portal 11. The completed ePRO survey forms 500 are then processed through data warehouse 8 and transactional data repository 12. For example, the ePRO survey forms 500 may be processed by the data ingest services 15. The audit trail 502 may be stored in the transactional data repository 12 along with a survey response table 504. The audit trail 502 may identify the survey, section, question, and response that was changed. The audit trail 502 may also track the previous value, who made the change, the time of the change, and a reason for the change. When a survey form 500 is edited, the audit trail 502 is attached to the updated survey and reprocessed through the data ingest services 15, which also updates the transactional data repository 12. For example, changes, updates, and soft delete transactions to ePRO data will be sent back to the data queue process, and then used to update the warehouse data and cubes and propagated to the customers. The following table includes data that may be included in the audit trail 502.

| Column name | Description |
| --- | --- |
| Audit ID | Unique ID for each entry/row |
| Study Name | Study the Questionnaire or form is associated with |
| Organization ID | Organization the Participant is associated with |
| Organization Name | Name of the Organization |
| Study Site ID | Study Site ID |
| Participant ID | Participant ID |
| Participant Name | Last Name, First Name |
| Questionnaire | The name of the Questionnaire that contains the edited item |
| Follow-up Number | The instance of a Questionnaire |
| Section Name | The section of the questionnaire that contains the edited item |
| Section Page Number | The section page # that contains the edited item |
| Row Number | For matrix questions - the row that contains the edited item |
| Question | Question associated with the edit |
| Response | The changed value |
| Audit Action | Created/Updated |
| Audit Change Reason | Reason entered for changing |
| Audit Time | Time the edit occurred dd-mmm-yyyy:hh:mm am/pm |
| User Role | Role of the user (at this study site) that made the edit |
| User Name | Last Name, First Name of user that made the edit |
| User Account Name | username of user that made the edit |

Audit trail reports 506 for individually selected questionnaires may contain the following information, displaying all edits for the selected questionnaire. This view may be shown whether selected by study personnel or participant.

| Column name | Description |
|---|---|
| Section Name | The section of the questionnaire that contains the edited item |
| Section Page Number | The section page # that contains the edited item |
| Row Number | For matrix questions - the row that contains the edited item |
| Question | Question associated with the edit |
| Response | The changed value |
| Audit Action | Created/Updated |
| Audit Time | Time the edit occurred dd-mmm-yyyy:hh:mm am/pm |
| User Name | Last Name, First Name of user that made the edit |

Additionally, the data in the ePRO survey forms 500 is processed by the data ingest services 15 and converted to JSON for storage in the data warehouse 8. The audit trails 502 may allow different users to not only view and process the most recent survey data, but to see how the data has been changed.

For example, a study manager may view the audit trail 502 of all questionnaires throughout the study to review and audit edits to questionnaires. The study manager may navigate to the reports dashboard, and select the audit report 506. The audit report 506 lists the audit trail 502 for all studies, all participants, all questionnaires. Any questionnaire or part of any questionnaire has associated audit trail line items.

As another example, a physician may view the audit trail 502 of a select participant and specific questionnaire to see if it has been edited. The physician may navigate to the site dashboard, choose a study site, select a participant, and a specific questionnaire, and select the audit trail icon. A dialog displays the audit trail 502 for the specific questionnaire chosen, and for each edited value, displays who, when, and why it was edited.

As another example a participant may view the audit trail 502 of a questionnaire for the participant to see if the questionnaire has been edited and by whom. The participant may navigate to the participant dashboard, and select the audit trail icon for a specific questionnaire. A dialog displays the audit trail 502 for the specific questionnaire chosen, and for each edited value, displays who, when, and why it was edited.

The research management system 100 may implement data security and privacy protection using data tagging. Data tagging may be defined as 'metadata that describes metadata.' With metadata described, the tags are used to categorize data at the metadata level. In an aspect, metadata describing data may be referred to as first metadata and data tags that describe metadata may be referred to as second metadata. For example, one use of data tagging is tagging participant metadata (e.g., participant name) and masking the data depending on the role viewing the tagged metadata. A physician for example may be allowed to view a participant's name, while an ePRO coordinator is not. For example, a customer (research entity) may want the patient name to be viewable by physicians, but want the patient name to be hidden from the ePRO Coordinator, to protect patient privacy while allowing study personnel to do their work. Accordingly, the participant name may be shown when a physician views the participant list but masked when an ePRO coordinator views the participant list. The following table shows example rules that may be applied to participant data fields based on role. Hide will hide the data as well as associated column, label, and facet. Mask will mask the data with "****", it will not hide the label or column, but will hide the facet. Show will show data, column, label, and facet as usual.

| Role | Participant ID | Participant Name | Participant Email |
|---|---|---|---|
| Physician | show | show | show |
| Nurse | show | show | show |
| EDC Coordinator | show | hide | hide |
| ePRO Coordinator | show | mask | mask |
| Data Manager | show | show | show |
| Organization Manager | show | show | show |
| Participant Manager | show | show | show |
| Personnel Manager | show | show | show |
| Participant & Personnel Manager | show | show | show |
| Study Manager | show | show | show |
| Content Manager | hide | hide | hide |
| Help Desk | hide | hide | hide |
| System Manager | show | show | show |

To accomplish the role based output using data tags, this example may use three tags, with the following associations and defaults.

| Tag | Participant ID | Participant Name | Participant Email |
|---|---|---|---|
| Pii_ID | hide | | |
| Pii_name | | mask | |
| Pii_email | | | hide |

Data tags will follow default data tag rules unless a specific role has overridden the default. For example, a help desk role may use tag default of 'hide'.

| Role | Pii_ID | Pii_name | Pii_email |
|---|---|---|---|
| Physician | show | show | show |
| Nurse | show | show | show |
| EDC Coordinator | show | hide | Default |
| ePRO Coordinator | show | Default | mask |
| Data Manager | show | show | show |
| Organization Manager | show | show | show |
| Participant Manager | show | show | show |
| Personnel Manager | show | show | show |
| Participant & Personnel Manager | show | show | show |
| Study Manager | show | show | show |
| Content Manager | Default | hide | Default |
| Help Desk | Default | hide | Default |
| System Manager | show | show | show |

Conflicts are resolved using access levels. Each tag rule has an associated access level to be used for conflicts. Although the example report does not illustrate multi-tag-conflicts, it is possible new users with multiple roles could be added, and would need the multi-role-conflicts resolved. When a role and data are both associated with the same (multiple) tags, there may be a conflict in tag rules. The tag rule with the lowest access level takes precedence. If a user has more than one role, there may be a conflict where the tag rule of one role conflicts with the tag rule of the other role. For display operation the study role rule with the highest access level takes precedence. If there is no study role for display, the study site role is evaluated on a per study-site basis where the highest access for data associated with that study-site takes precedence. For faceted search operations the role with the lowest number takes precedence. In the event the user turns off column sorting, the lowest number takes precedence. In the event there are both multi-role and multi-tag conflicts, the multi-role conflict is resolved first, then the multi-tag conflict is resolved. The following table shows example rules and access level values.

| Access Level | Rule | Description |
| --- | --- | --- |
| 30 | show | Show the data value |
| 20 | mask | Mask the data value with "****" |
| 10 | hide | Data is blank |

Any field can be tagged using a field tag The elements of a field tag are described in the table below.

| FieldTag | Elements |
| --- | --- |
| FieldIdentifier | unique value identifying the field |
| TagName | Name of Tag |
| TagValue | Default Tag Value |

Figure 7:
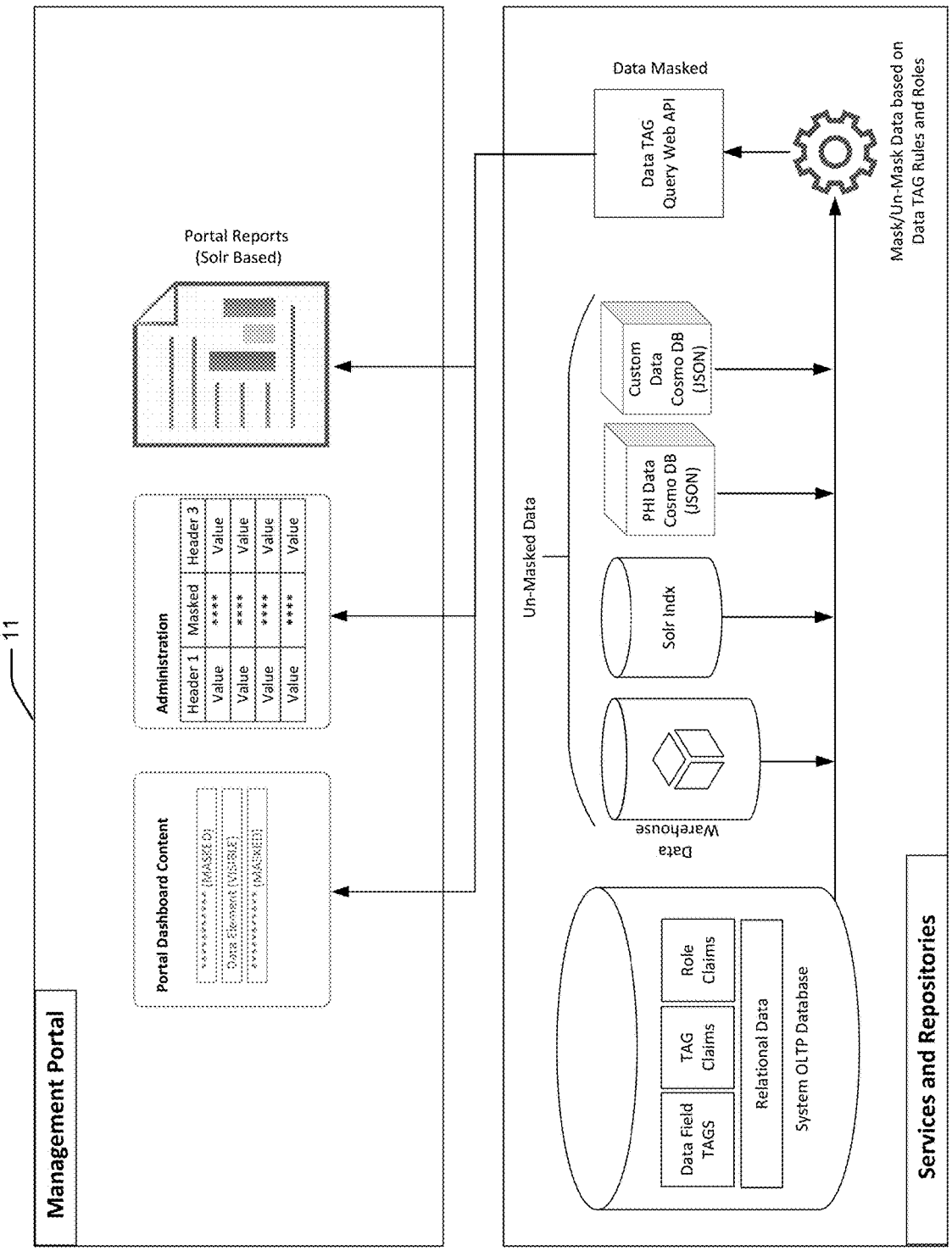
FIG. 7 is a schematic diagram of an example architecture for tagging data, according to an aspect of the disclosure.

FIG. 7 illustrates an example architecture for implementing data tagging. The relevant tagged data may be stored in the transactional data repository 12. Additional data may be stored in the data warehouse 8, Solr Index, and a Cosmo D8 database. When a report is generated via the management portal 11 (e.g., using a query), the management portal 11 performs a mask/unmask function based on data tag rules and roles. For example, the management portal 11 may check the user's claim(s) based on the tag name & value. The tag name & value serve to describe the field(s) that have that name/value pair. Users have claim(s) based on the name/value pair. For example, a user will have a claim to fields that are tagged PHI:true. This claim may be "show", "hide", or "mask". When the management portal 11 loads the data, the management portal 11 performs these steps on the server: 1) Identify the fields in the data that are tagged; 2) Get the user's claim(s) to the tagged fields; 3) Enforce the user's claim(s)—for "hide" and "mask", the management portal 11 modifies the underlying data; and 4) Return the modified data to the user.

Figure 8:
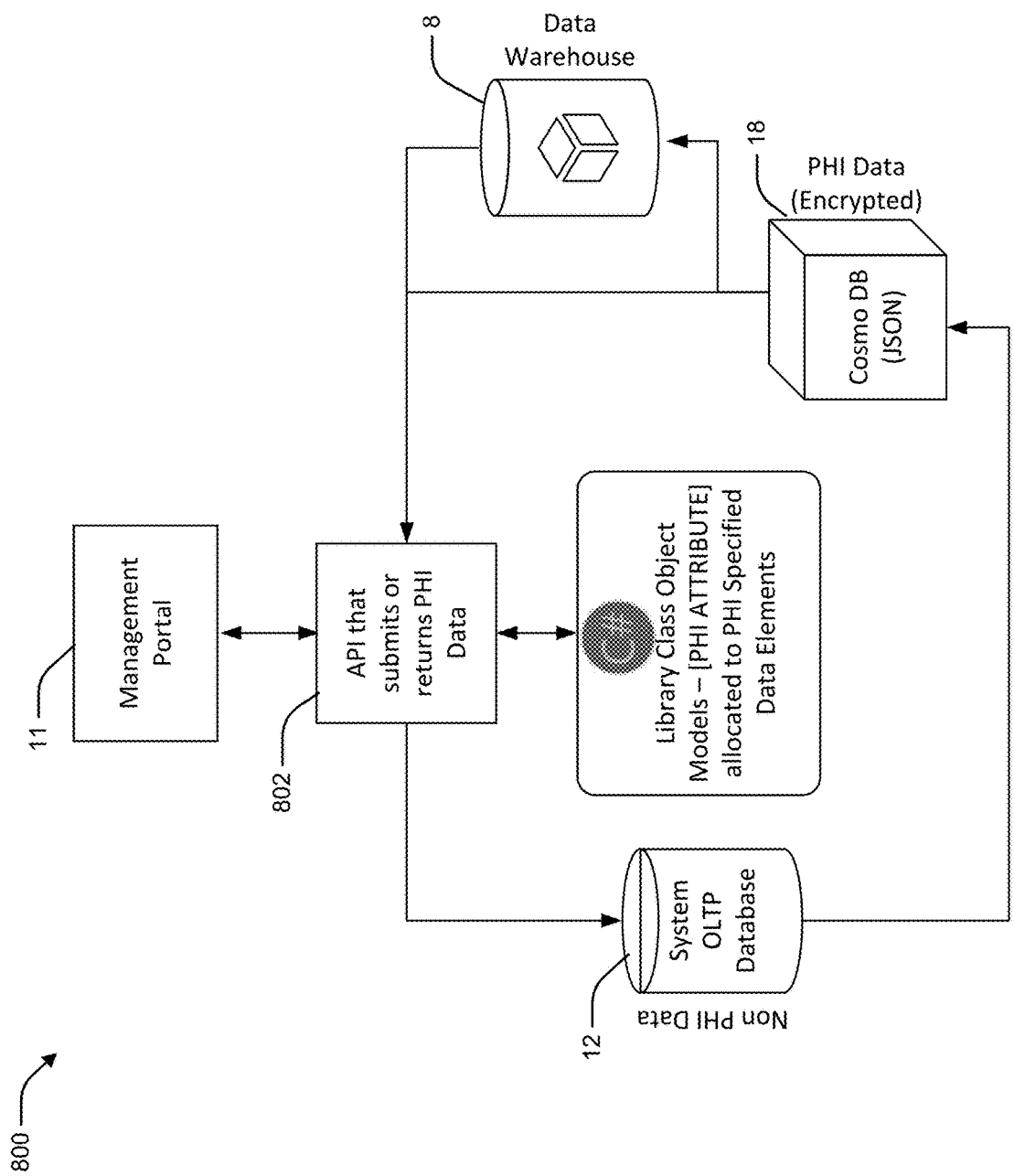
FIG. 8 is a schematic diagram of an example architecture for managing protected health information (PHI), according to an aspect of the disclosure.

In an aspect, protected health information (PHI) is segregated from other data. FIG. 8 illustrates an example architecture 800 for storing PHI. PHI may be stored in a Cosmos database 18, where the PHI is encrypted at rest. The management portal 11 may implement an API 802 that links the PHI with other data in response to a request from a user interface (e.g., a reporting module). The management portal 11 may implement role based security on the PHI to ensure only authorized users receive the PHI. For example, the API 802 may acquire non-PHI data from the transactional data repository 12, and use pointers from the transactional data repository 12 to query the Cosmos database 18 for the PHI.

In an aspect, the research management system 100 may provide video analysis and analytics processing to support enhanced facial redaction, redaction editing, and family support models. Video data may be collected from a mobile application, which may be considered a data provider 1. The video may be collected as part of a research study. For example, the mobile application may instruct a caregiver to record a video of a patient performing a specific action. The research management system 100 may perform facial redaction processing on the video to obscure the face of the patient in the video.

Figure 9:
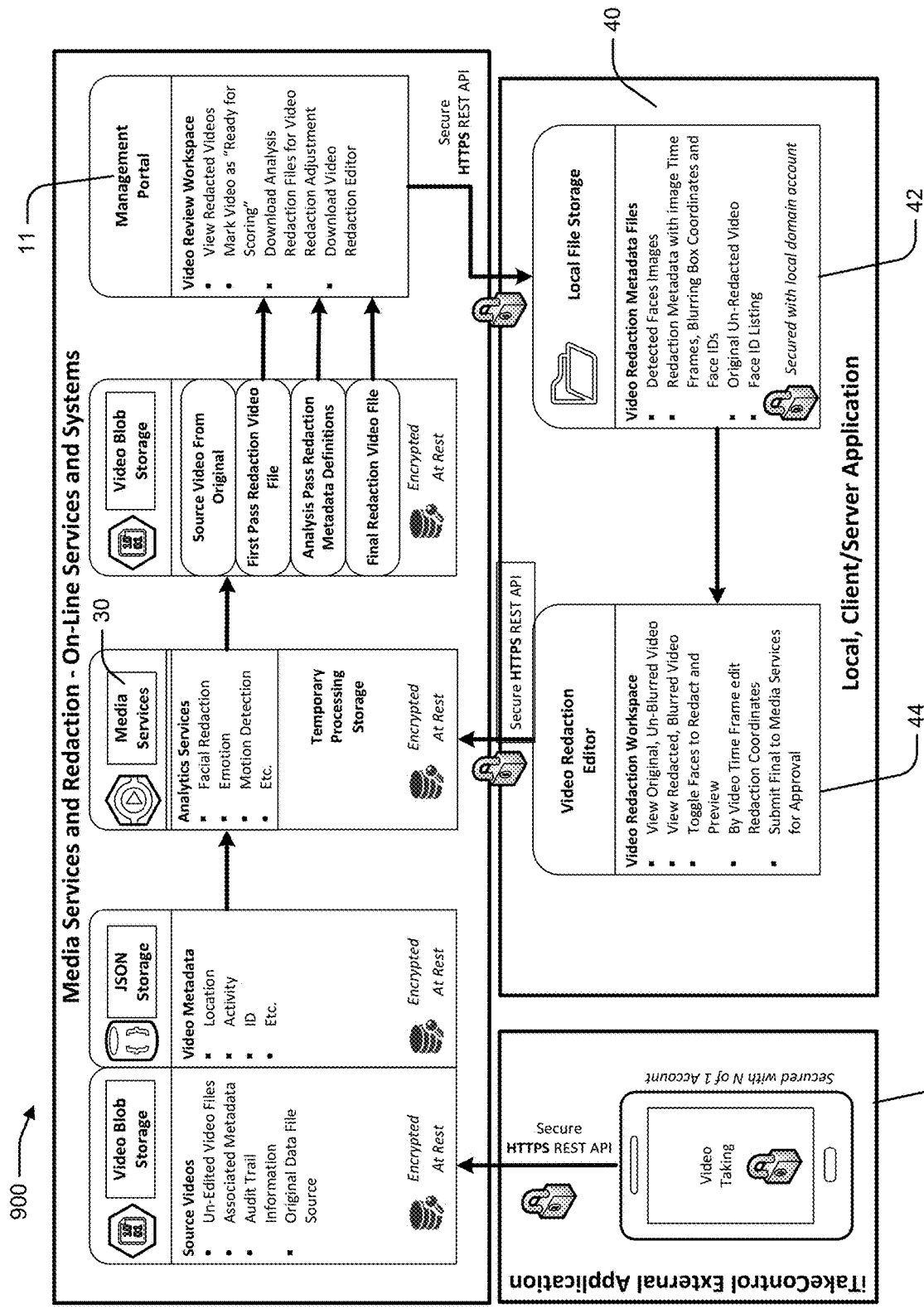
FIG. 9 is a schematic diagram of an example architecture for managing videos for redaction, according to an aspect of the disclosure.

FIG. 9 illustrates an architecture 900 for processing video data. The raw video data may be transmitted from the mobile application 902 to the research management system 100 via a secure connection such as an HTTPS REST API. The research management system 100 may ingest the raw video data using the data ingest services 15 and store the video in the document repository 6 as a video blob with associated metadata. A media services module 30 may indicate video processing services to be performed on the video blob. The management portal 11 may be used to initiate video processing using a video processing application 60. The video processing application 60 may include a local file storage 62 including video redaction metadata files. The video redaction metadata files may include detected facial images, redaction metadata identifying image time frames, blurring box coordinates, and face IDs. A redaction editor 44 may be used to manage video redaction. For example, the redaction editor 44 may be used to view raw videos, view redacted videos, toggle faces to redact and view, edit blurring coordinates, and submit final redacted videos.

Figure 10:
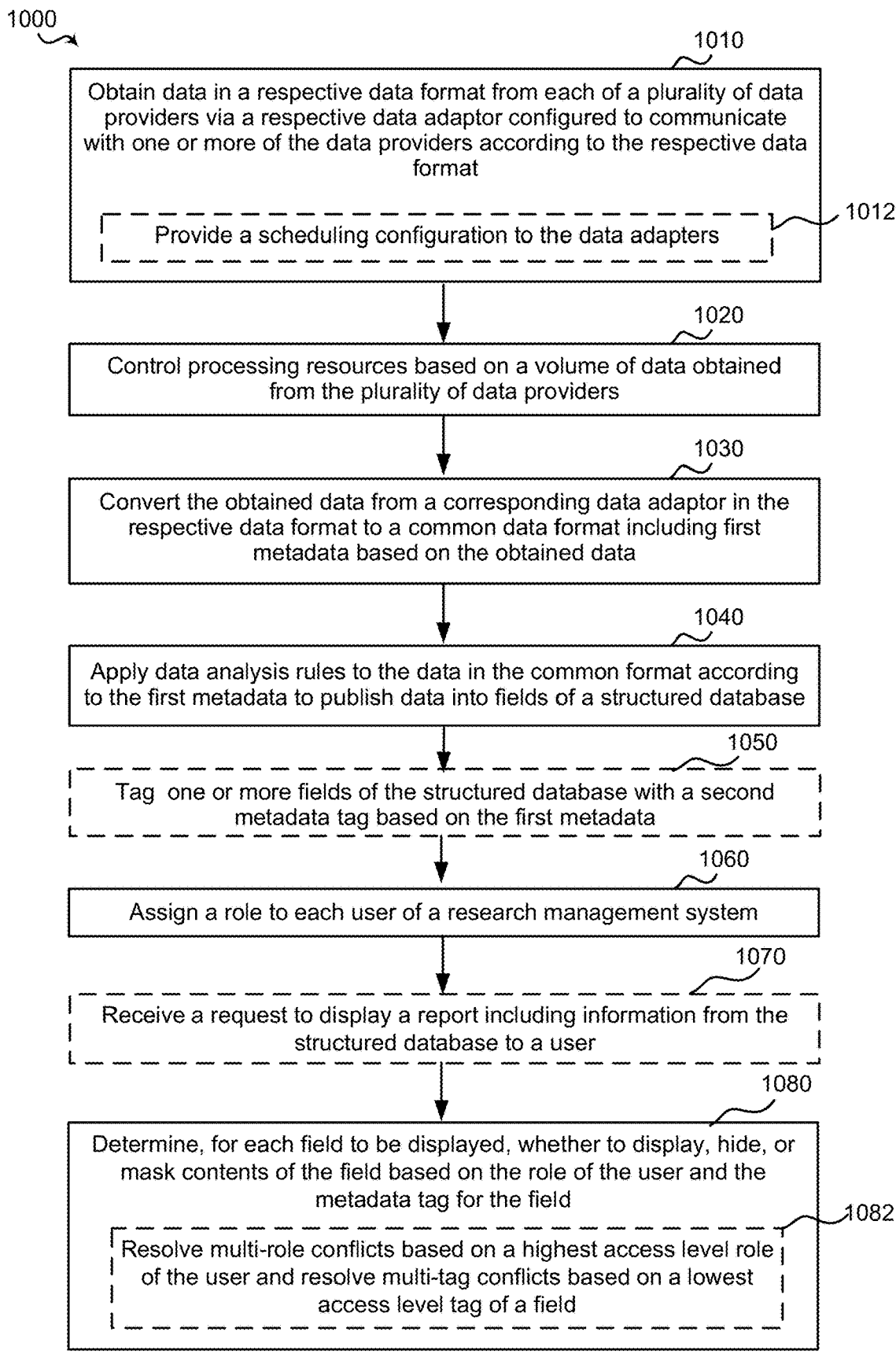
FIG. 10 is a flowchart showing an example method of managing medical research data.

FIG. 10 is a flowchart of a method 1000 of managing medical study data. The method 1000 may be performed by the research management system 100. It is understood that the specific order or hierarchy of blocks in the processes/flowcharts disclosed is an illustration of exemplary approaches. Based upon design preferences, it is understood that the specific order or hierarchy of blocks in the processes/flowcharts may be rearranged. Further, some blocks may be combined or omitted. The accompanying method claims present elements of the various blocks in a sample order, and are not meant to be limited to the specific order or hierarchy presented.

In block 1010, the method 1000 may include obtaining data in a respective data format from each of a plurality of data providers via a respective data adaptor configured to communicate with one or more of the data providers according to the respective data format. In an aspect, for example, each data adaptor 2 may obtain the data in the respective data format from one or more respective data providers 1. In an aspect, the data may be medical research records such as ePRO or EDC documents. In sub-block 1012, the block 1010 may include providing a scheduling configuration to the data adapters. In an aspect, for example, the data processor 3 may provide the scheduling configuration to the data adaptors. The scheduling configuration may indicate a schedule for the data providers 1 to provide the data to the data adaptors 2.

In block 1020, the method 1000 may include controlling processing resources based on a volume of data obtained from the plurality of data providers. In an aspect, for example, the data processor 3 may control the processing resources based on the volume of data obtained from the plurality of data providers 1. For example, controlling the processing resources may include increasing or decreasing cloud resources used for processing the obtained data.

In block 1030, the method 1000 may include converting the obtained data from a corresponding data adaptor in the respective data format to a common data format including first metadata based on the obtained data. In an aspect, for example, the data converters 4 may convert the obtained data from a corresponding data adaptor in the respective data format to a common data format including the first metadata based on the obtained data.

In block 1040, the method 1000 may include applying data analysis rules to the data in the common format according to the metadata to publish data into fields of a structured database. In an aspect, for example, the data pipelines 7 may apply the data analysis rules to the data in the common format according to the metadata to publish data into fields of a structured database.

In block 1050, the method 1000 may include tagging one or more fields of the structured database with a second metadata tag based on the first metadata. In an aspect, for example, the data pipelines 7 may tag the one or more fields of the records with the second metadata tag. The second metadata may describe the first metadata. For example, the first metadata may identify a type of the data. The data pipelines 7 may use the first metadata to determine which field of the structured database to publish the data to. The data pipelines 7 may also determine an access level based on the first metadata and tag the data with a second metadata tag. The second metadata tag may indicate an access level for viewing the content of the field.

In block 1060, the method 1000 may include assigning a role to each user of a research management system. In an aspect, for example, the disease management portal 11 may assign the role to each user of the research management system 100. The disease management portal 11 may be configured by a study manager to assign other roles based on criteria used to register with the research management system 100.

In block 1070, the method 1000 may include receiving a request to display a report including information from the structured database to one of the users. In an aspect, for example, the disease management portal 11 may receive the request to display the report including information from the records to one of the users. For instance, the request may be a request to generate or view a report.

In block 1080, the method 1000 may include determining, for each field to be displayed, whether to display, hide, or mask contents of the field based on the role of the user and the second metadata tag for the field. In an aspect, for example, the disease management portal 11 may determine, for each field to be displayed, whether to display, hide, or mask contents of the field based on the role of the user and the second metadata tag for the field. For example, in sub-block 1082, the block 1080 may include resolving multi-role conflicts based on a highest access level role of the user and resolving multi-tag conflicts based on a lowest access level tag of a field. For example, the disease management portal 11 may resolve the multi-role conflicts and the multi-tag conflicts.

Figure 11:
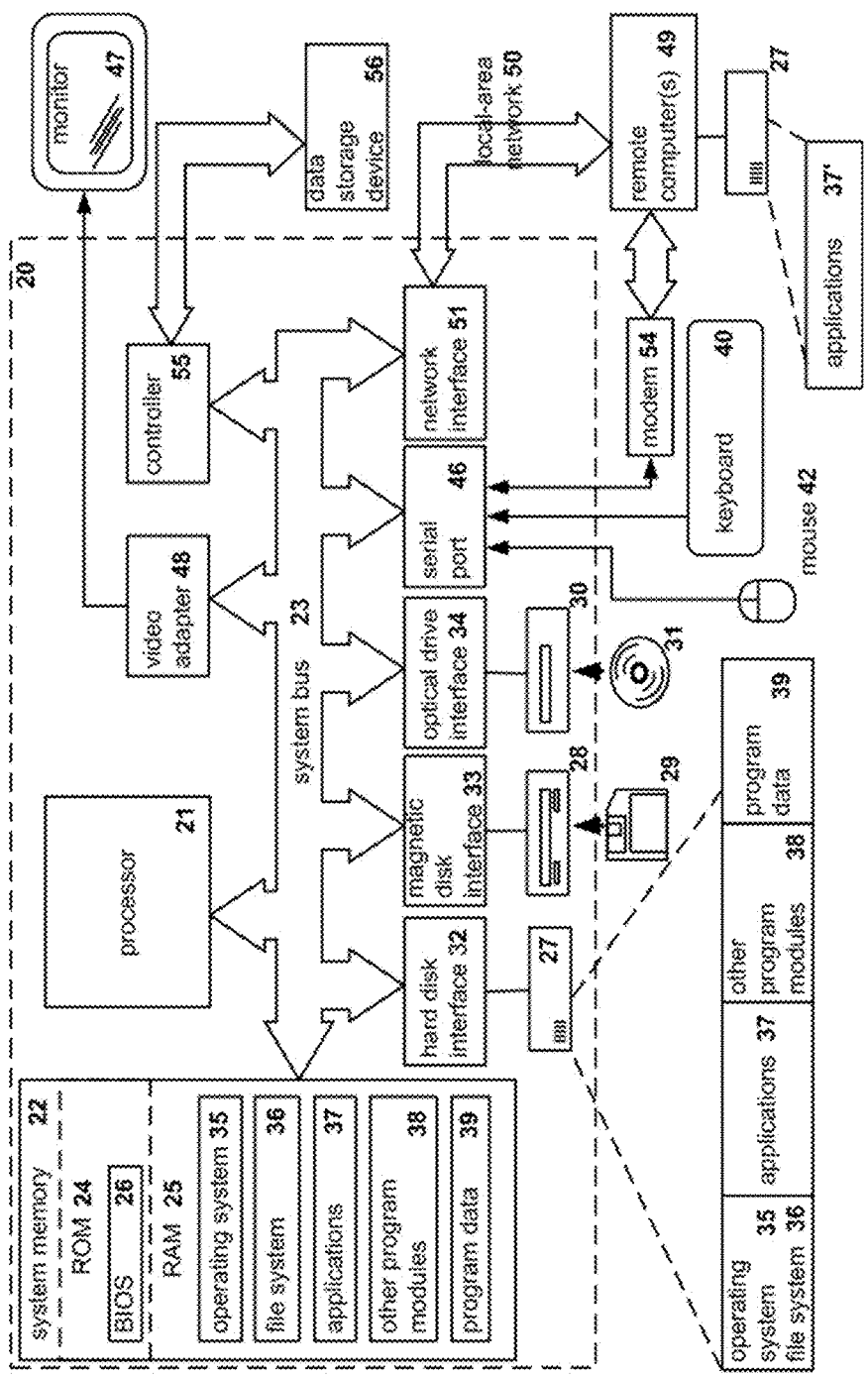
FIG. 11 is a schematic diagram of an example computer system.

FIG. 11 illustrates a block diagram of an example of a general-purpose computer system on which the disclosed system and method can be implemented according to an example aspect. As shown, a general purpose computing device is provided in the form of a computer system 20 or the like including a processing unit 21, a system memory 22, and a system bus 23 that couples various system components including the system memory to the processing unit 21. It should be appreciated that computer system 20 can correspond to computing device 120 described above, processing unit 21 can correspond to the CPU 810, and system memory 22 can correspond to memory 812 according to various exemplary aspects.

Moreover, the system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system 26 (BIOS), containing the basic routines that help transfer information between elements within the computer 20, such as during start-up, is stored in ROM 24.

The computer 20 may further include the hard disk drive 27 for reading from and writing to a hard disk, a magnetic disk drive 28 for reading from or writing to a removable magnetic disk 29, and an optical disk drive 30 for reading from or writing to a removable optical disk 31 such as a CD-ROM, DVD-ROM or other optical media. The hard disk drive 27, magnetic disk drive 28, and optical disk drive 30 are connected to the system bus 23 by a hard disk drive interface 32, a magnetic disk drive interface 33, and an optical drive interface 34, respectively. The drives and their associated computer-readable media provide non-volatile storage of computer readable instructions, data structures, program modules and other data for the computer 20.

A number of program modules may be stored on the hard disk, magnetic disk 29, optical disk 31, ROM 24 or RAM 25, including an operating system 35. The computer 20 includes a file system 36 associated with or included within the operating system 35, one or more application programs 37, other program modules 38 and program data 39. A user may enter commands and information into the computer 20 through input devices such as a keyboard 40 (which can correspond to display 860) and pointing device 42. Other input devices (not shown) may include a microphone, joystick, game pad, satellite dish, scanner or the like.

These and other input devices are often connected to the processing unit 21 through a serial port interface 46 that is coupled to the system bus, but may be connected by other interfaces, such as a parallel port, game port or universal serial bus (USB). A monitor 47 or other type of display device is also connected to the system bus 23 via an interface, such as a video adapter 48. In addition to the monitor 47, personal computers typically include other peripheral output devices (not shown), such as speakers and printers.

The computer 20 may operate in a networked environment using logical connections to one or more remote computers 49. The remote computer (or computers) 49 may be another computer, a server (e.g., servers 24A to 24N), a router, a network PC, a peer device, physical equipment and/or other common network node, and typically includes many or all of the elements described above relative to the computer 20. The logical connections include a network interface or adapter 53 and connected to a local area network (i.e., LAN) 51, for example, and/or a wide area network (not shown). Such networking environments are commonplace in offices, enterprise-wide computer networks, Intranets and the Internet.

When used in a LAN networking environment, the computer 20 is connected to the local network 51 through a network interface or adapter 53. When used in a WAN networking environment, the computer 20 typically includes a modem 54 or other means for establishing communications over the wide area network, such as the Internet. Moreover, the modem 54, which may be internal or external, is connected to the system bus 23 via the serial port interface 46. In a networked environment, program modules depicted relative to the computer 20, or portions thereof, may be stored in the remote memory storage device. It will be appreciated that the network connections shown are exemplary and other means of establishing a communications link between the computers may be used.

In various aspects, the systems and methods described herein may be implemented in software, in which the methods may be stored as one or more instructions or code on a non-volatile computer-readable medium. Computer-readable medium includes data storage. By way of example, and not limitation, such computer-readable medium can comprise RAM, ROM, EEPROM, CD-ROM, Flash memory or other types of electric, magnetic, or optical storage medium, or any other medium that can be used to carry or store desired program code in the form of instructions or data structures and that can be accessed by a processor of a general purpose computer.

The invention claimed is:

1. A computer system for managing medical research data, comprising:
   a network interface connecting the computer system to a plurality of data providers that provide a plurality of data schemas and transmission mechanisms for providing clinical and real-world data in a plurality of different data formats and that relates to medical research participants;
   a plurality of data adaptors that are each configured to communicate with one or more of the data providers to obtain the clinical and real-world data in the respective data formats;
   a plurality of data converters executed by processing resources, with each data converter configured to convert the clinical and real-world data from a corresponding data adaptor in the respective data format to a common data format that is labeled with first metadata associating the clinical and real-world data to the respective medical research participants;
   a data repository for storing medical research records of the clinical and real-world data as unstructured raw data, with each medical research record including transaction metadata that provides details of a transaction timing, content type and source of the clinical and real-world data for the medical research record relating to the respective medical research participants, such that each medical record is configured to be independently accessible based on a unique metadata schema even after a change in the respective data format of the plurality of data schemas;
   at least one data pipeline configured to query the data repository to parse the unstructured raw data using the transaction metadata to obtain at least one document and to publish the unstructured raw data resulting from the at least one document into fields of a structured database, wherein the data pipeline tags at least one field in the structured database with display control metadata; and
   a management portal configured to:
      assign a role to each user of the computer system;
      receive a request to display a report including a portion of the fields of the structure database; and
      for each field to be displayed in the report, determine whether to display, hide, or mask contents of the respective field based on the role of the user and the display control metadata of the field.

2. The computer system of claim 1, wherein the data adaptors are modules configured for processing the clinical and real-world data in a respective data format obtained via a respective interchange mechanism.

3. The computer system of claim 1, wherein a data processor provides scheduling configuration services to the data adapters, wherein the scheduling configuration indicates a schedule for the corresponding data provider to provide the clinical and real-world data.

4. The computer system of claim 1, wherein the processing resources are distributed cloud services, and wherein the data processor provides a dashboard interface including a chart of total processing rate by time, a chart of utilization of the distributed cloud services, and a measure of utilization cost.

5. The computer system of claim 1, wherein the common data format is a JavaScript Object Notation (JSON) object including a key and an unstructured data portion.

6. The computer system of claim 1, wherein the display control metadata indicates an access level based on first metadata indicating the content type of the unstructured raw data.

7. The computer system of claim 1, further comprising an analytics server configured to generate pre-defined data cubes based on the structured database.

8. The computer system of claim 1, wherein the role of each user includes at least roles of: participant, physician, and study manager.

9. The computer system of claim 8, wherein the participant role is associated with a family model including a parent role that is allowed to generate documents on behalf of the associated participant role and generate documents for the parent role.

10. The computer system of claim 8, wherein the management portal is configured to resolve multi-role conflicts based on a highest access level of the user and resolve multi-tag conflicts based on a lowest access level tag of a field.

11. A method of controlling access to medical research data, comprising:
    receiving, from a plurality of data providers that provide a plurality of data schemas and transmission mechanisms, clinical and real-world data in a plurality of different data formats and that relates to medical research participants;
    obtaining, by a plurality of data adaptors, the clinical and real-world data in the respective data formats;
    converting, by a plurality of data converters, the clinical and real-world data from a corresponding data adaptor in the respective data format to a common data format that is labeled with first metadata associating the clinical and real-world data to the respective medical research participants;
    storing, in a data repository, medical research records of the clinical and real-world data as unstructured raw data, with each medical research record including transaction metadata that provides details of a transaction timing, content type and source of the clinical and real-world data for the medical research record relating to the respective medical research participants, such that each medical record is configured to be independently accessible based on a unique metadata schema even after a change in the respective data format of the plurality of data schemas;
    querying, by at least one data pipeline, the data repository to parse the unstructured raw data using the transaction metadata to obtain at least one document and publishing the unstructured raw data resulting from the at least one document into fields of a structured database;
    tagging, by the at least one data pipeline, each of the fields with display control metadata;
    assigning a role to each user of a research management system;
    receiving a request to display a report including a portion of the fields of the structure database; and
    for each field to be displayed in the report, determining whether to display, hide, or mask contents of the respective field based on the role of the user and the display control metadata for the field.

12. The method of claim 11, wherein the role of each user includes at least roles of: participant, physician, and study manager.

13. The method of claim 12, wherein a participant role is associated with a family model including a parent role that is allowed to generate documents on behalf of the associated participant role and generate documents for the parent role.

14. The method of claim 11, wherein determining whether to display, hide, or mask contents of the field comprises resolving multi-role conflicts based on a highest access level role of the user and resolving multi-tag conflicts based on a lowest access level tag of a field.

15. The method of claim 11, wherein the data adaptors are modules configured for processing a respective data format obtained via a respective interchange mechanism.

16. The method of claim 11, further comprising providing a scheduling configuration to the data adapters, wherein the scheduling configuration indicates a schedule for the corresponding data provider to provide the clinical and real-world data.

17. The method of claim 11, further comprising executing the plurality of data converters by processing resources that are distributed cloud services, and wherein controlling the processing resources comprises providing dashboard interface including a chart of total processing rate by time, a chart of utilization of the distributed cloud services, and a measure of utilization cost.

18. The method of claim 14, further comprising storing the medical research records to include at least one pre-defined data cube including at least one protected health information field having a metadata tag with an access level that hides or masks the protected health information field from study personnel roles.

19. A computer system for managing medical research data, the computer system comprising:
  a network interface connecting the computer system to a plurality of data providers that provide a plurality of data schemas and transmission mechanisms for providing clinical and real-world data in a plurality of different data formats and that relates to medical research participants;
  a plurality of data adaptors that are each configured to communicate with one or more of the data providers to obtain the clinical and real-world data in the respective data formats;
  a plurality of data converters executed by processing resources, with each data converter configured to convert the clinical and real-world data from a corresponding data adaptor in the respective data format to a common data format that is labeled with first metadata associating the respective medical research participants;
  a data repository for storing medical research records of the clinical and real-world data as unstructured raw data, with each medical research record including transaction metadata that provides details of a transaction timing, content type and source of the clinical and real-world data for the medical research record relating to the respective medical research participants, such that each medical record is configured to be independently accessible based on a unique metadata schema even after a change in the respective data format of the plurality of data schemas;
  at least one data pipeline configured to: (i) query the data repository to parse the unstructured raw data using the transaction metadata to obtain at least one document and to publish the unstructured raw data resulting from the at least one document into fields of a structured database configured to be displayed in a requested report, and (ii) tag at least one field in the structured database with display control metadata; and
  a management portal configured to:
    determine a role to each user of the computer system;
    receive a request from a respective user to display a report including a portion of the fields of the structure database; and
    for each field to be displayed in the report, determine whether to display, hide, or mask contents of the respective field based on the role of the respective user and the display control metadata.

\* \* \* \* \*